US006665556B1

(12) United States Patent
Alfano et al.

(10) Patent No.: US 6,665,556 B1
(45) Date of Patent: Dec. 16, 2003

(54) METHOD AND APPARATUS FOR EXAMINING A TISSUE USING THE SPECTRAL WING EMISSION THEREFROM INDUCED BY VISIBLE TO INFRARED PHOTOEXCITATION

(76) Inventors: Robert R. Alfano, 3777 Independence Ave., Bronx, NY (US) 10463; Stavros G. Demos, 3550 Pacific Ave., Apt. 304, Livermore, CA (US) 94550; Gang Zhang, 3 Rieder Rd., Edison, NJ (US) 08817

( * ) Notice: Subject to any disclaimer, the term of this patent is extended or adjusted under 35 U.S.C. 154(b) by 0 days.

(21) Appl. No.: 09/493,939

(22) Filed: Jan. 28, 2000

Related U.S. Application Data
(60) Provisional application No. 60/117,761, filed on Jan. 29, 1999.

(51) Int. Cl.[7] .................................................. A61B 6/00
(52) U.S. Cl. ...................... 600/473; 600/476; 600/474; 600/477
(58) Field of Search ................................ 600/425, 473, 600/475, 476, 477; 436/63, 64

(56) References Cited

U.S. PATENT DOCUMENTS

| | | | |
|---|---|---|---|
| 4,810,875 A | * 3/1989 | Wyatt | |
| 4,930,516 A | 6/1990 | Alfano et al. | |
| 4,947,850 A | * 8/1990 | Vanderkooi et al. | |
| 5,131,398 A | 7/1992 | Alfano et al. | |
| 5,261,410 A | 11/1993 | Alfano et al. | |
| 5,348,018 A | 9/1994 | Alfano et al. | |
| 5,383,452 A | * 1/1995 | Buchert | 600/347 |
| 5,413,108 A | 5/1995 | Alfano | |
| 5,467,767 A | * 11/1995 | Alfano et al. | |
| 5,582,168 A | * 12/1996 | Samuels et al. | |
| 5,612,540 A | 3/1997 | Richards-Kortum et al. | |
| 5,813,987 A | * 9/1998 | Modell et al. | |
| 5,879,294 A | * 3/1999 | Anderson et al. | |
| 6,055,451 A | * 4/2000 | Bambot et al. | |
| 6,091,983 A | * 7/2000 | Alfano et al. | |

OTHER PUBLICATIONS

Zhang et al., "Far–red and NIR Spectral Wing Emission from Tissues under 532 and 632 nm Photo–excitation," Lasers in the Life Sciences, 9:1–16 (1999).
Hanlon et al., "Near–infrared Fluorescence Spectroscopy Detects Alzheimer's Disease in Vitro," Photochem. and Photobiol., 70(2):236–42 (1999).
Zhang et al., "Far–red and NIR emission from tissues," SPIE, 3250:72–7 (1999).

* cited by examiner

*Primary Examiner*—George Manuel
*Assistant Examiner*—Runa Shah Qaderi
(74) *Attorney, Agent, or Firm*—Cohen, Pontani, Lieberman & Pavane

(57) ABSTRACT

Method and an apparatus for examining a tissue using the spectral wing emission therefrom induced by visible to infrared photoexcitation. In one aspect, the method is used to characterize the condition of a tissue sample and comprises the steps of (a) photoexciting the tissue sample with substantially monochromatic light having a wavelength of at least 600 nm; and (b) using the resultant far red and near infrared spectral wing emission (SW) emitted from the tissue sample to characterize the condition of the tissue sample. In one embodiment, the substantially monochromatic photoexciting light is a continuous beam of light, and the resultant steady-state far red and near infrared SW emission from the tissue sample is used to characterize the condition of the tissue sample. In another embodiment, the substantially monochromatic photoexciting light is a light pulse, and the resultant time-resolved far red and near infrared SW emission emitted from the tissue sample is used to characterize the condition of the tissue sample. In still another embodiment, the substantially monochromatic photoexciting light is a polarized light pulse, and the parallel and perpendicular components of the resultant polarized time-resolved SW emission emitted from the tissue sample are used to characterize the condition of the tissue sample.

37 Claims, 17 Drawing Sheets

METHOD AND APPARATUS FOR EXAMINING A TISSUE USING THE SPECTRAL WING EMISSION THEREFROM INDUCED BY VISIBLE TO INFRARED PHOTOEXCITATION

CROSS-REFERENCE TO RELATED APPLICATIONS

The present application claims the benefit under 35 U.S.C. §119(e) of U.S. Provisional Patent Application Serial No. 60/117,761, filed Jan. 29, 1999, the disclosure of which is incorporated herein by reference.

BACKGROUND OF THE INVENTION

The present invention relates generally to the examination of tissues using optical spectroscopy and relates more particularly to a method and an apparatus for examining a tissue using the spectral wing emission therefrom induced by visible to infrared photoexcitation.

Optical spectroscopy has received increasing attention over the past several years as a tool for use in examining tissues. One such application of optical spectroscopy to the examination of tissues has been in the detection of cancer and precancerous states and has involved the use of steady-state native fluorescence. For example, in U.S. Pat. No. 4,930,516, inventors Alfano et al., which issued Jun. 5, 1990, and which is incorporated herein by reference, there is disclosed a method and apparatus for detecting the presence of cancerous tissue using visible luminescence. According to the aforementioned patent, the tissue to be examined is excited with a beam of monochromatic light that causes the tissue to fluoresce over a spectrum of wavelengths. The monochromatic light disclosed in the patent has a wavelength in the range of 350–500 nm. The intensity at which the excited tissue fluoresces is measured either over a spectrum or at a predetermined number of preselected wavelengths, such as at 531 nm, 522 nm and 633 nm. The patent further teaches that one can then determine the carcinomatoid status of the tissue in question by comparing the detected spectrum, one or more peak wavelengths of the detected spectrum, or a ratio or difference of particular wavelengths from the detected spectrum to standards obtained from known tissues.

Another example of the use of optical spectroscopy, particularly steady-state native fluorescence, in the detection of cancer and precancerous states is disclosed in U.S. Pat. No. 5,131,398, inventors Alfano et al., which issued Jul. 21, 1992, and which is incorporated herein by reference. In the aforementioned patent, there is disclosed a method and apparatus for distinguishing cancerous tumors and tissue from benign tumors and tissue or normal tissue using native fluorescence. According to one embodiment of said patent, the tissue to be examined is excited with a beam of monochromatic light at 300 nm. The intensity of the native fluorescence emitted from the tissue is measured at 340 nm and at 440 nm. The ratio of the two intensities is then calculated and used as a basis for determining if the tissue is cancerous as opposed to benign or normal. According to another embodiment of said patent, excitation profiles may be employed to distinguish cancerous tissue from benign or normal tissue. For example, the patent teaches that excitation spectra obtained by measuring the intensity of fluorescence at 340 nm as the excitation wavelength is varied from 220 nm to 325 nm are different for cancerous and benign breast tissues.

Other patents and publications that relate to the use of steady-state native fluorescence in the detection of cancer and precancerous states include the following: U.S. Pat. No. 5,042,494, inventor Alfano, issued Aug. 27, 1991; U.S. Pat. No. 5,413,108, inventor Alfano, issued May 9, 1995; U.S. Pat. No. 5,769,081, inventors Alfano et al., issued Jun. 23, 1998; U.S. Pat. No. 5,612,540, inventors Richards-Kortum et al., issued Mar. 18, 1997; U.S. Pat. No. 4,957,114, inventors Zeng et al., issued Sep. 18, 1990; Yang et al., "Fundamental Differences of Excitation Spectrum between Malignant and Benign Breast Tissues," *Photochemistry and Photobiology*, 66(4):518–22 (1997); Yang et al., "Excitation Spectrum of Malignant and Benign Breast Tissues: A Potential Optical Biopsy Approach," *Lasers in the Life Sciences*, 7(4):249–65 (1997); Galeotti et al., "On the Fluorescence of NAD(P)H in Whole-Cell Preparations of Tumours and Normal Tissues," *Eur. J. Biochem.*, 17:485–96 (1970); and Japanese Patent Application No. Sho-57–795, published Jul. 15, 1983, all of which are incorporated herein by reference.

In addition, it should be noted that steady-state native fluorescence has also been used to detect a number of other abnormal or disease states unrelated to cancer, such as the detection of caries in teeth (U.S. Pat. No. 4,479,499, inventor Alfano, which issued Oct. 30, 1984, and which is incorporated herein by reference) and the detection of atherosclerotic plaque in arteries (U.S. Pat. No. 4,913,142, inventors Kittrell et al., issued Apr. 3, 1990, and which is incorporated herein by reference).

Another type of technique for detecting cancer in tissues has involved the use of time-resolved fluorescence spectroscopy and is exemplified by U.S. Pat. No. 5,348,018, inventors Alfano et al., which issued Sep. 20, 1994, and U.S. Pat. No. 5,467,767, inventors Alfano et al., which issued Nov. 21, 1995, both of which are incorporated herein by reference. In, for example, the aforementioned U.S. Pat. No. 5,348,018, there is disclosed a method for determining if tissue is malignant as opposed to non-malignant (i.e., benign tumor tissue, benign tissue, or normal tissue), said method comprising, in one embodiment, irradiating a human breast tissue sample with light at a wavelength of about 310 nm and measuring the time-resolved fluorescence emitted therefrom at about 340 nm. The time-resolved fluorescence profile is then compared to similar profiles obtained from known malignant and non-malignant human breast tissues. By fitting the profiles to the formula $I(t)=A_1 e^{(-t/\tau 1)}+A_2 e^{(-t/\tau 2)}$, one can quantify the differences between tissues of various conditions. For example, non-malignant human breast tissues exhibit a slow component ($\tau_2$) which is less than 1.6 ns whereas malignant human breast tissues exhibit a slow component ($\tau_2$) which is greater than 1.6 ns. In addition, non-malignant human breast tissues exhibit a ratio of fast to slow amplitudes ($A_1/A_2$) which is greater than 0.85 whereas malignant human breast tissue exhibit a ratio of fast to slow amplitudes ($A_1/A_2$) which is less than 0.6. This technique can be used with different excitation and/or emission wavelengths, and can be applied to the detection of malignancies (or other abnormal states) in tissues other than human breast tissue.

It should be noted that conventional fluorescence spectroscopic techniques of the types described above for detecting cancerous or precancerous states in tissues, whether of the steady-state variety or of the time-resolved variety, have typically involved using photoexcitation wavelengths far below 600 nm, said photoexcitation wavelengths typically residing in the range of about 300 to 500 nm.

Another type of spectroscopic technique that has been used to examine tissues has involved the use of Raman spectroscopy. One such application of Raman spectroscopy to the examination of tissues has been in the detection of cancer and is exemplified by U.S. Pat. No. 5,261,410, inventors Alfano et al., which issued Nov. 16, 1993, and which is incorporated herein by reference. In the aforementioned patent, there is disclosed a method for determining if a tissue is a malignant tumor tissue, a benign tumor tissue, or a normal or benign tissue. The method is based on the discovery that, when irradiated with a beam of infrared monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1078, 1300, 1445 and 1651 $cm^{-1}$ for normal or benign tissue, the presence of three Raman bands at a Raman shift of about 1240, 1445 and 1659 $cm^{-1}$ for benign tumor tissue, and the presence of two Raman bands at a Raman shift of about 1445 and 1651 $cm^{-1}$ for malignant tumor tissue. In addition, it was discovered that for human breast tissue the ratio of intensities of the Raman bands at a Raman shift of about 1445 and 1659 $cm^{-1}$ is about 1.25 for normal or benign tissue, about 0.93 for benign tumor tissue, and about 0.87 for malignant tumor tissue.

In addition, as exemplified by U.S. Pat. No. 5,293,872, inventors Alfano et al., which issued Mar. 15, 1994, and which is incorporated herein by reference, Raman spectroscopy has also been used to distinguish between calcified atherosclerotic tissue and fibrous atherosclerotic tissue or normal cardiovascular tissue.

It should be noted that conventional Raman spectroscopic techniques of the types described above have typically involved using photoexcitation wavelengths in the range of about 680 nm to 1350 nm.

When using Raman spectroscopy to examine tissues, there is often detected, in addition to the desired Raman bands, an undesired fluorescence emission, which appears as background and is typically regarded as noise. Typically, the longer the photoexcitation wavelength, the smaller the fluorescence emission detected. See Frank et al., "Characterization of human breast specimens with Near-IR Raman spectroscopy," Anal. Chem., 66(3):319–26 (1994), which is incorporated herein by reference. More specifically, where the photoexcitation wavelength is in much of the visible portion of the spectrum, the fluorescence is generally so large from the tissue that the Raman signature lines are not visible. Where, however, the photoexcitation wavelength is longer, e.g., in the range of about 632 nm to 980 nm, the Raman lines are usually visible, but the fluorescence emission is typically stronger than the Raman emission. However, because the fluorescence emission in this situation is typically regarded as noise since it is the Raman emission that is of interest, complex fitting parameters have been devised to subtract that portion of the detected signal attributable to fluorescence emission in order to identify those spectral features associated with the Raman active vibration modes. See Baraga et al., "Rapid near-infrared Raman spectroscopy of human tissue with a spectrograph and CCD detector," Appl. Spectrosc., 46(2):187–90 (1992) and Mahadevan et al., "Optical techniques for the diagnosis of cervical precancers: Comparison of Raman and fluorescence spectroscopies," in Advances in Fluorescence Sensing Technology II, J. R. Lakowicz, ed., Proc. SPIE, 2388:110–20 (1995), both of which are incorporated herein by reference.

Accordingly, in view of the above, it can be seen that far red and near infrared spectral wing (SW) emissions, where incidentally induced by photoexcitation of tissues with light having a wavelength of at least 600 nm, have not heretofore been used to detect cancerous tissues or other abnormal or diseased tissue states, such as diabetics, Alzheimers, sleep disorders, aging, lung disorders, blood flow, bile-ruben infection, burns, and SW emission wavelengths are at least 20 nm more than the excitation wavelength.

SUMMARY OF THE INVENTION

It is an object of the present invention to provide a new method for examining a tissue.

It is another object of the present invention to provide a new method for examining a tissue that involves the use of the spectral wing emission from the tissue induced by visible (in particular, visible having a wavelength greater than about 600 nm) to infrared photoexcitation of the tissue.

It is yet another object of the present invention to provide a method as described above that can be used for either in vivo or in vitro examination of a tissue.

Therefore, according to one aspect of the invention, there is provided a method for characterizing the condition of a tissue sample (i.e., characterizing the tissue sample as normal, cancerous, precancerous, adipose, etc.), said method comprising the steps of: (a) photoexciting the tissue sample with substantially monochromatic light having a wavelength of at least 600 nm; and (b) using the resultant far red and near infrared spectral wing emitted from the tissue sample to characterize the condition of the tissue sample for emission wavelength>650 nm.

In one embodiment, the substantially monochromatic photoexciting light is a continuous beam of light and said using step comprises using the resultant steady-state native far red and near infrared spectral wing emitted from the tissue sample to characterize the condition of the tissue sample. Preferably, the photoexciting light has a wavelength in the range of about 600 to 980 nm. The SW emission wavelength is at least 20 nm greater than the excitation wavelength (for example, excite with 630 nm and measure SW from 650 nm to 950 nm). Said using step may comprise obtaining a spectral profile of the steady-state far red and near infrared spectral wing emitted from the tissue sample and comparing said spectral profile to standards obtained from tissues whose conditions are known. This may be done, for example, by determining the normalized integrated intensity of the spectral profile and comparing said normalized integrated intensity to appropriate standards or by determining a ratio or difference of intensities at two wavelengths along said spectral profile and comparing said ratio or difference to appropriate standards. Said using step may alternatively comprise detecting the resultant steady-state far red and near infared spectral wing emission at two wavelengths (instead of along a spectrum), determining a ratio or difference of intensities at said two wavelengths and comparing said ratio or difference to appropriate standards.

In another embodiment, the substantially monochromatic photoexciting light is a light pulse and said using step comprises using the resultant time-resolved far red and near infrared spectral wing emitted from the tissue sample to characterize the condition of the tissue sample. Preferably, the photoexciting light has a wavelength in the range of about 600 to 980 nm. The SW emission wavelength is at least 20 nm greater than excitation wavelength (for example, excite with 800 nm and SW emission wavelengths are from 840 nm to 950 nm). Said using step may comprise obtaining a profile of the time-resolved SW emitted from the tissue sample and comparing said profile to standards obtained from tissues whose conditions are known. This may be done, for example, by fitting the time-resolved profile to the formula $I(t)=A_1 e^{(-t/\tau_1)}+A_2 e^{(-t/\tau_2)}$ and comparing the resultant values for $A_1/A_2$ and/or $\tau_1$ with appropriate standards.

In still, another embodiment, the substantially monochromatic photoexciting light is a polarized light pulse and said using step comprises using the parallel and perpendicular components of the resultant polarized time-resolved far red and near infrared spectral wing emitted from the tissue sample to characterize the condition of the tissue sample. Preferably, the photoexciting light has a wavelength in the range of about 600 to 980 nm. Said using step may comprise obtaining a profile of one or both of the parallel and perpendicular components of the polarized time-resolved far red and near infrared spectral wing emitted from the tissue sample and comparing said profile(s) to standards obtained from tissues whose conditions are known. This may be done, for example, by fitting the time-resolved profile(s) to the formula $I(t)=A_1 e^{(-t/\tau 1)}+A_2 e^{(-t/\tau 2)}$ and comparing the resultant values with appropriate standards.

According to another aspect of the invention, there is provided a method for imaging a tissue sample, said method comprising the steps of: (a) photoexciting the tissue sample with substantially monochromatic light having a wavelength of at least 600 nm; and (b) using the resultant far red and near infrared spectral wing emitted from the tissue sample to form an image of the tissue sample from 650 nm to 950 nm.

It is even yet another object of the present invention to provide a new apparatus for imaging a tissue.

It is still yet another object of the present invention to provide a new apparatus for imaging a tissue that involves the use of the spectral wing emission from the tissue induced by far red (in particular, visible having a wavelength greater than about 600 nm) to infrared photoexcitation of the tissue.

It is a further object of the present invention to provide an apparatus as described above that can be used for the in vivo or in vitro imaging of a tissue.

Therefore, according to another aspect of the invention, there is provided an apparatus for imaging a tissue sample, said apparatus comprising: (a) a light source for photoexciting the tissue sample with substantially monochromatic light having a wavelength of at least 600 nm; (b) a light detector; (c) collection optics for imaging the light emitted from the tissue sample from 650 nm to 950 nm onto the light detector; (d) filter means positioned between the tissue sample and the light detector for selectively transmitting, from the light emitted from the tissue sample, light having a wavelength greater than said substantially monochromatic light by at least 20 nm; and (e) a display coupled to said light detector for displaying an image of the tissue sample based on the light detected by said light detector.

Preferably, said apparatus is further provided with the instrumentalities needed to perform one or more of the techniques described above for characterizing the condition of a tissue. In this manner, one can both image a tissue and indicate (for example, by a scheme of shading or coloring) the condition of the tissue.

Additional objects, as well as features, advantages and aspects of the present invention, will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate a preferred embodiment of the invention and, together with the description, serve to explain the principles of the invention. In the drawings wherein like reference letters and numerals represent like parts.

DETAILED DESCRIPTION OF PREFERRED EMBODIMENTS

The present invention is based on the unexpected discovery that the spectral wing emissions from different tissue types (e.g., cancer, precancer, normal, fat) induced by visible (specifically, at least 600 nm) to infrared photoexcitation are distinguishable from one another and can be used to characterize a tissue whose condition is unknown.

Figure 1:
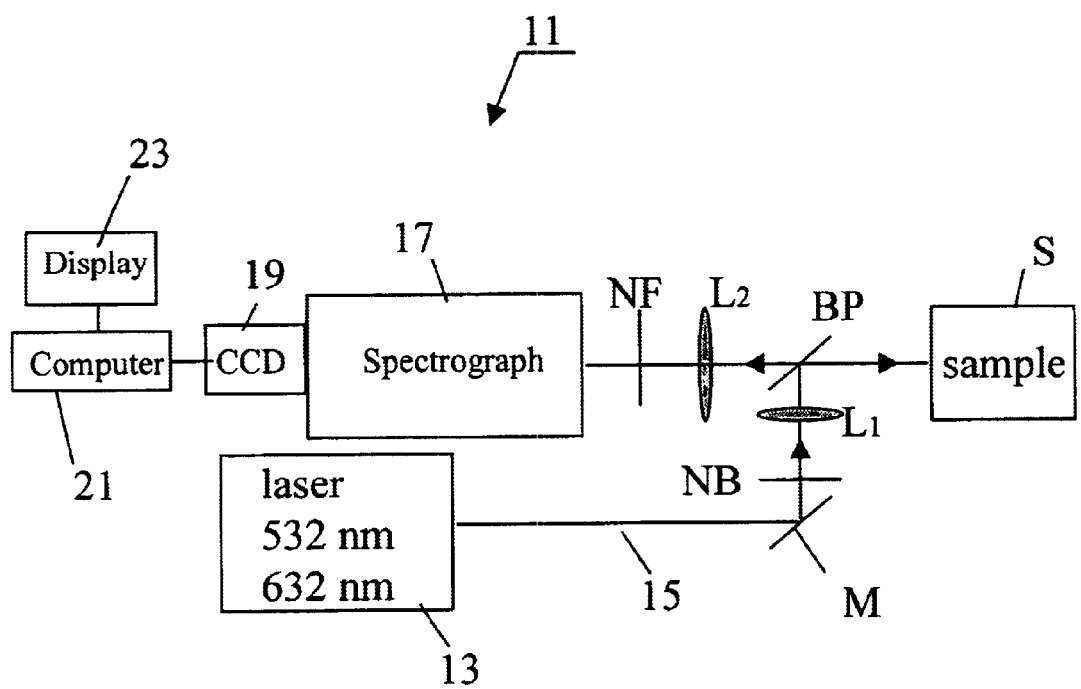
FIG. 1 is a schematic diagram of a first experimental setup used to perform a first embodiment of the method of the present invention.

Referring now to FIG. 1, there is shown a schematic diagram of a first experimental setup used to perform a first embodiment of the method of the present invention, said first experimental setup being constructed according to the teachings of the present invention and being represented by reference numeral 11.

Setup 11 comprises a laser system 13 for emitting laser light along a path 15, laser system 13 comprising a mode-locked Nd:YAG laser, a pulse compressor, and a synchronously pumped dye laser. Both the 532 nm, 4 ps frequency doubled output of the Nd:YAG laser and the 632 nm, 500 fs output of the dye laser have an average power of a few mW. The intensity of the laser beams is kept low in order to avoid two-photon or multistep photo-excitation phenomena. (Laser system 13 may further or alternatively include a single mode 50 mW diode laser operated at 800 nm.)

The laser light traveling along path 15 is reflected by a mirror M and then passed through a narrow band filter NB to ensure monochromatic illumination. (Obviously, two different narrow band filters need to be used depending upon whether one is illuminating at 532 nm or at 632 nm.) The laser light is then focused by a 20 cm focal length lens $L_1$ onto the tissue sample S (after being reflected off a beam splitter BP).

The light emitted from the tissue sample S is then collected in a back-scattering geometry by an 85 mm focal length camera lens $L_2$ (after being transmitted through beam splitter BP) and passed through a laser line notch filter NF to remove scattered laser light. The light passed through notch filter NF is then coupled into the 0.1 mm slit of a quarter meter spectrograph 17 (ARC SpectroPro 275), where it is spectrally analyzed, and then is recorded by a CCD camera 19 (Princeton Instrument Model No. TE/CCD-512SF). The output of camera 19 is coupled to a computer 21 for processing, and the output of computer 21 is displayed on a display 23, which may be a monitor and/or a printer.

The samples examined with setup 11 included adipose and breast chicken tissues obtained from a local market and normal and cancerous human breast tissues obtained from NDRI (National Disease Research Interchange). Pairs of cancerous and normal human breast tissue samples taken from the same patient were used from 12 different patients. The tissue samples were not chemically treated and were not frozen prior to our experimental measurements. The tissue samples were kept in the refrigerator at temperatures 2–4° C. The different tissue components were separated and homogenous parts were selected and positioned inside a 1×1 $cm^2$ quartz cell. All measurements were performed at room temperature.

Figure 2A:
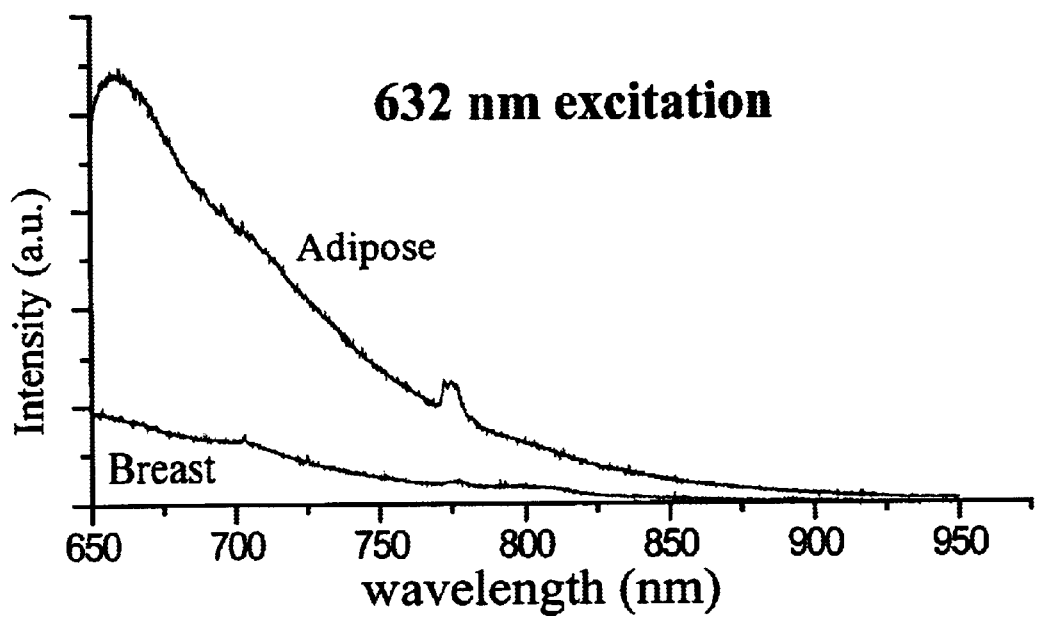
FIGS. 2(a) and 2(b) are graphic representations of the steady-state far-red and near-infrared spectral wing (SW) emission spectra (650–950 nm) resulting from 632 and 532 nm laser excitation, respectively, of adipose and breast chicken tissue samples using the experimental setup of FIG. 1.
Figure 2B:
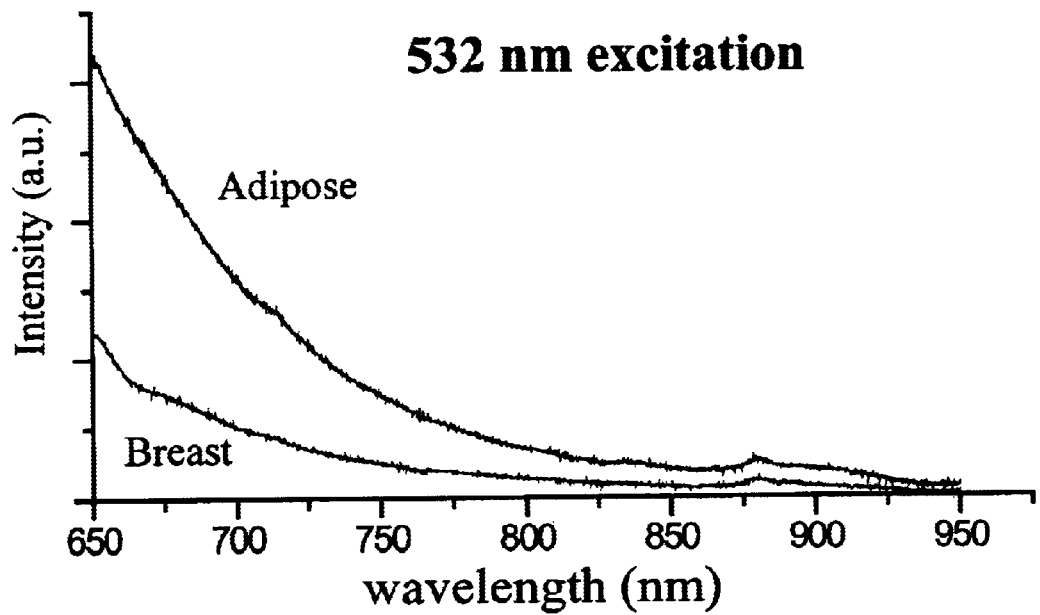

Referring now to FIGS. 2(a) and 2(b), there can be seen the steady-state far-red and near-infrared spectral wing (SW) emission spectra (650–950 nm) resulting from 632 and 532 nm laser excitation, respectively, of the above-described adipose and breast chicken tissue samples using setup 11. As can be seen, these spectra show that the adipose tissue exhibits stronger emission than the breast chicken tissue under identical illuminating conditions. The ratio of the integrated emission intensities of adipose to breast tissue is approximately 4:1 under 632 nm illumination while the same intensity ratio under 532 nm excitation is approximately 3:1. The emission spectra under 632 nm illumination shown in FIG. 2(a) indicate the presence of several weak peaks around 720 and 780 nm arising from Raman scattering. The peak observed at 660 nm is an artifact due to the notch filter. The spectral profiles from the two types of tissues under 532 nm excitation shown in FIG. 2(b) are very similar with their intensity decreasing rapidly at longer wavelengths. A small peak is observed centered at ≈870 nm for both types of tissue under 532 nm illumination.

Figure 3A:
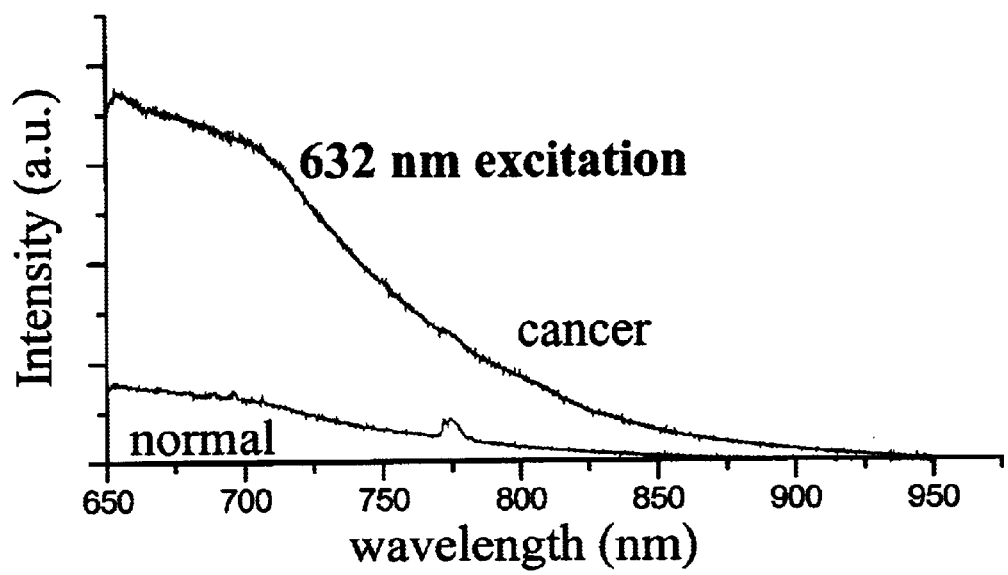
FIGS. 3(a) and 3(b) are graphic representations of the steady-state far-red and near-infrared spectral wing (SW) emission spectra (650–950 nm) resulting from 632 and 532 nm laser excitation, respectively, of cancerous and normal human breast tissue samples using the experimental setup of FIG. 1.
Figure 3B:
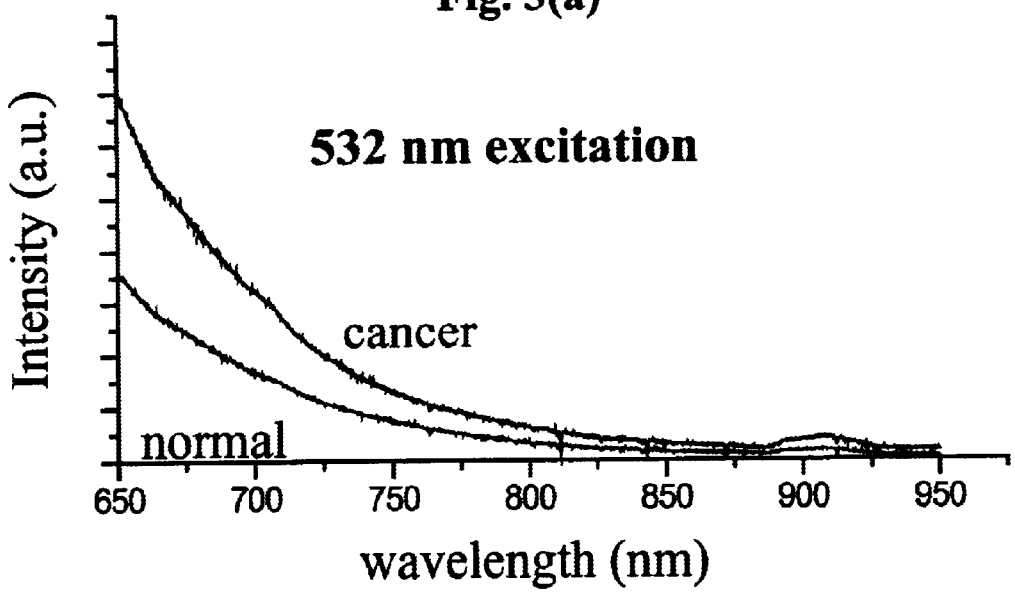

Referring now to FIGS. 3(a) and 3(b), there can be seen the steady-state far-red and near-infrared spectral wing (SW) emission spectra (650–950 nm) resulting from 632 and 532 nm laser excitation, respectively, of the above-described normal and cancerous human breast tissue samples using setup 11. As can be seen, these spectra show that the cancerous tissue exhibits stronger emission than the normal tissue under identical illuminating conditions. The ratio of the integrated intensities of the emission from cancer over the intensity from normal tissue is approximately 4.5 under 632 nm excitation and approximately 2 under 532 nm excitation. The Raman scattering spectral components are superimposed onto the much stronger emission background and they contribute very little in the measured ratio of the integrated intensities.

Figure 4:
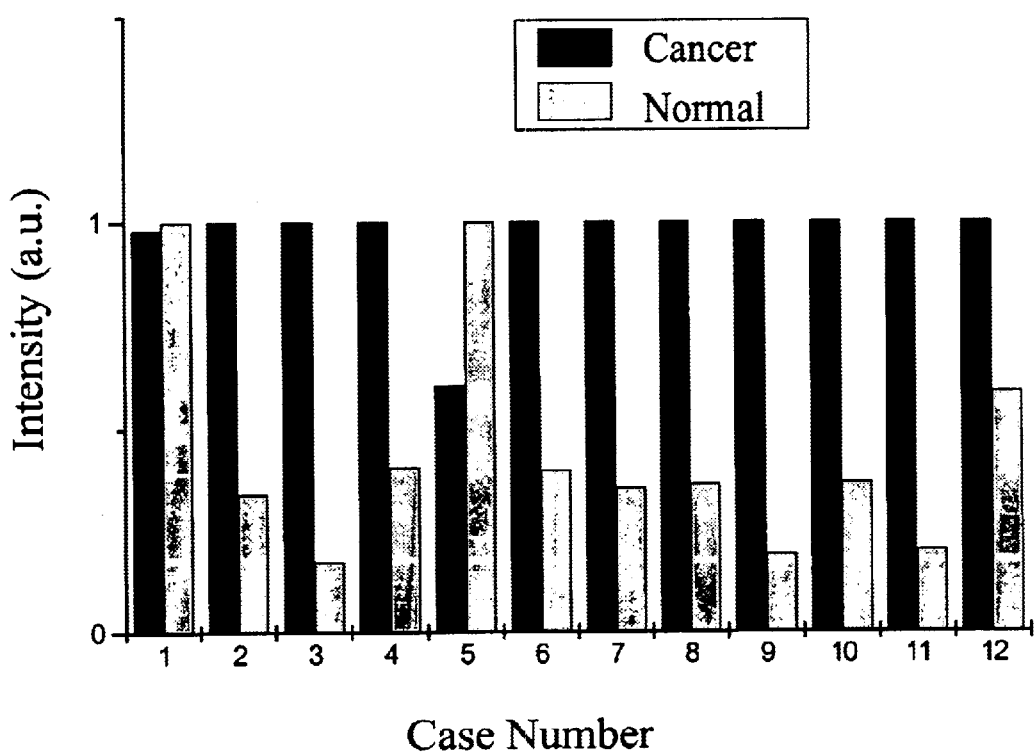
FIG. 4 is a bar chart showing the normalized integrated intensities of the far-red emission from cancerous and normal human breast tissues under 632 nm excitation using the experimental setup of FIG. 1.

Referring now to FIG. 4, there can be seen a bar chart showing the normalized to peak integrated intensity far-red emission (650–950 nm) under 632 excitation from normal and cancerous tissue samples obtained from 12 patients. These results show that, in the samples obtained from 10 patients, the integrated intensity of the emission is stronger for the cancerous sample than in the normal tissue sample. These data suggest that the integrated far-red emission intensity could be used to distinguish between normal and cancerous tissue components of human breast. It is notable that in 9 of the 12 patients, the integrated intensities of the far-red emission of the cancerous samples were about two-fold or more times stronger than from the corresponding normal tissue sample from the same patient. These results indicate the presence of a systematic enhanced intensity in the cancer tissue sample when compared to normal tissue. For these 12 patients studied, in 10 cases the far-red emission from the cancer sample was greater than from the normal sample, in one case the intensity was approximately the same while only in one case the result was inconsistent. In more than 75% of the cases, the intensity from the tumor tissue was twofold or more higher than from the normal tissue. A statistical analysis of the experimental integrated intensity from the 12 patients shows a significant difference between normal and cancer tissue samples with p=0.002 in the pair t-test. See Glantz, *Primer of Biostatistics*, $3^{rd}$ ed., McGraw-Hill, Inc. (1992), which is incorporated herein by reference.

Figure 5A:
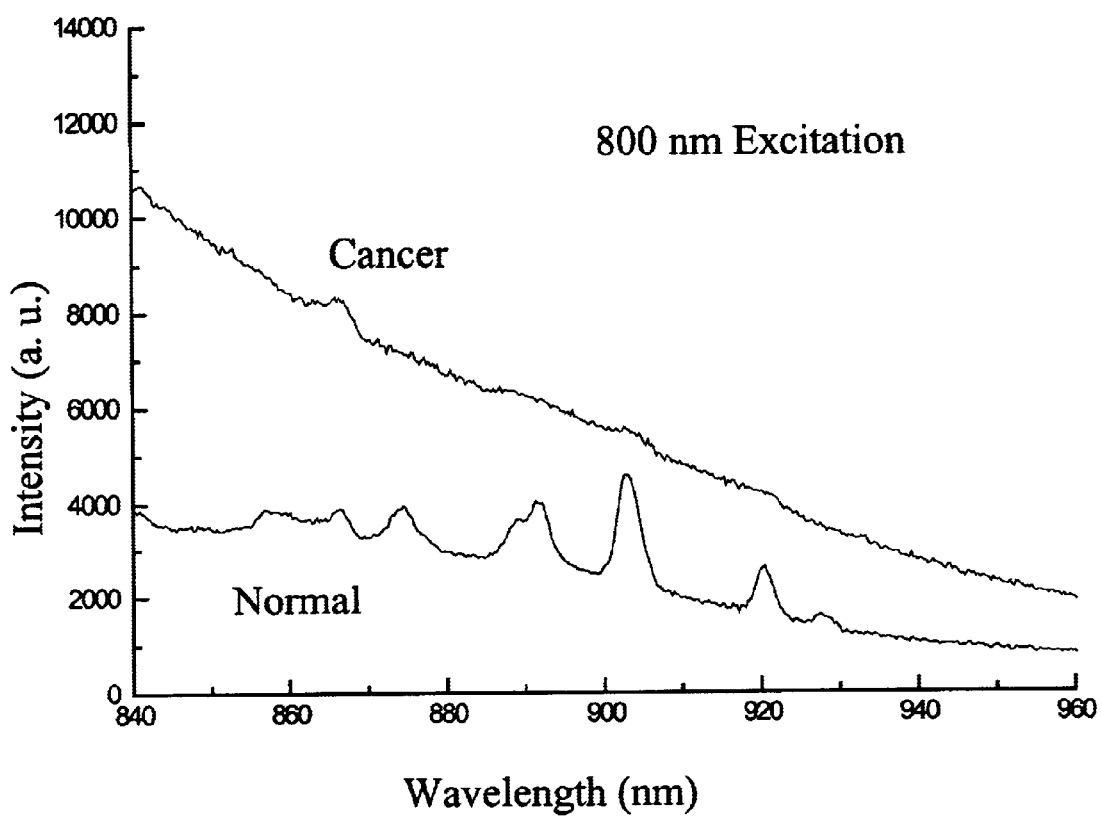
FIG. 5(a) is a graphic representation of the NIR steady-state emission spectra of normal and cancerous human breast tissue samples following excitation at 800 nm.

Referring now to FIG. 5(a), there are shown NIR steady-state emission spectra (with Raman lines) of normal and cancerous human breast tissue samples from 840 nm to 960 nm following excitation under identical illumination conditions with a single mode 50 mW diode laser operated at 800 nm. (Setup 11 was used, except for the replacement of laser system 13 with the aforementioned diode laser and except for the use of narrow band and notch filters appropriate for use with said diode laser.) As can be seen, the spectral wing intensity is stronger in the cancerous sample than in the normal sample. In fact, the ratio of the integrated emission intensities for the cancerous tissue to the normal tissues is approximately 2:1, respectively. As can also be seen, the Raman lines are much stronger in the normal sample profile than in the cancerous sample profile. It is believed that the stronger Raman lines in the normal sample profile are attributable primarily to fat components in the normal tissue sample.

Another discovery of the present invention is that the intensity of the spectral wing emission from tissues following illumination with light having a wavelength of at least 600 nm increases with an increase in temperature (a linear relationship between intensity and temperature being apparent from 58° C. to 97° C.). This relationship was established in the following manner: Muscle samples from chicken legs and chicken breasts were purchased from a local market and considered as homogeneous (on a macroscopic level) biological test media. After the fat and tendon tissues were taken out completely, the samples were mounted in a specially designed 4 mm diameter and 1 mm deep aluminum sample-holder used for the heating bath and spectral analysis. The heating bath was produced by the circulation of pre-warmed 0.9% saline solution in a water bath (Fisher Scientific, Model 9101, Pittsburgh, Pa.) for 5 min. The temperature stability was ±0.01° C. The temperature was increased from 37° C. to 49° C. and from 61° C. to 97° C. in 6° C. steps and from 49° C. to 61° C. in 3° C. steps. Six groups of samples from different chickens were investigated. At each temperature level, six target sites were measured in each group. After cooling down to room temperature in saline solution (10 min. after heat treatment), the samples moistened with saline solution were mounted in the sample-holder and placed between quartz and aluminum slides for spectral emission intensity and scattering intensity studies. The measurement process was finished within 30 min. after heating. The temperature of the measuring environment was 25° C.

Figure 5B:
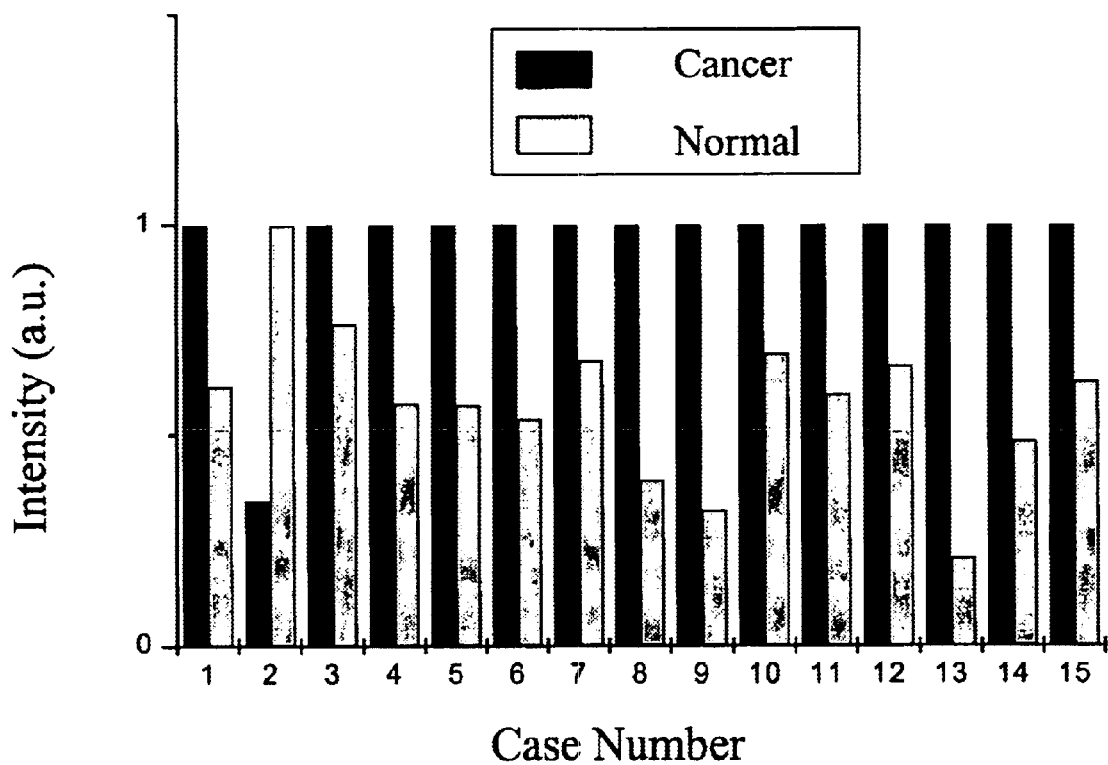
FIG. 5(b) is a bar chart showing the normalized integrated intensities of the far-red emission from tumor and normal human breast under 800 nm excitation for 15 different patients.

The statistic bar graph of the normalized to peak integrated intensity far red SW emission from normal and cancer tissue samples shows the comparison results from different patients under 632 and 800 nm laser excitation in FIG. 5(b). Under 800 nm excitation, the integrated SW emission intensities (obtained in range of 825~965 nm) from cancer sample in 14 patients are stronger than from normal samples obtained from 15 patients shown in FIG. 5(b). These data suggest that the integrated far-red emission SW intensity could be used to separate normal and cancer tissue components of human breast. Under 800 nm excitation, it is characteristic that in 12 of the 15 patients, the integrated intensities of the far-red emission of the cancer samples were about 50% or more times stronger than from the corresponding normal tissue sample from the same patient.

Figure 6:
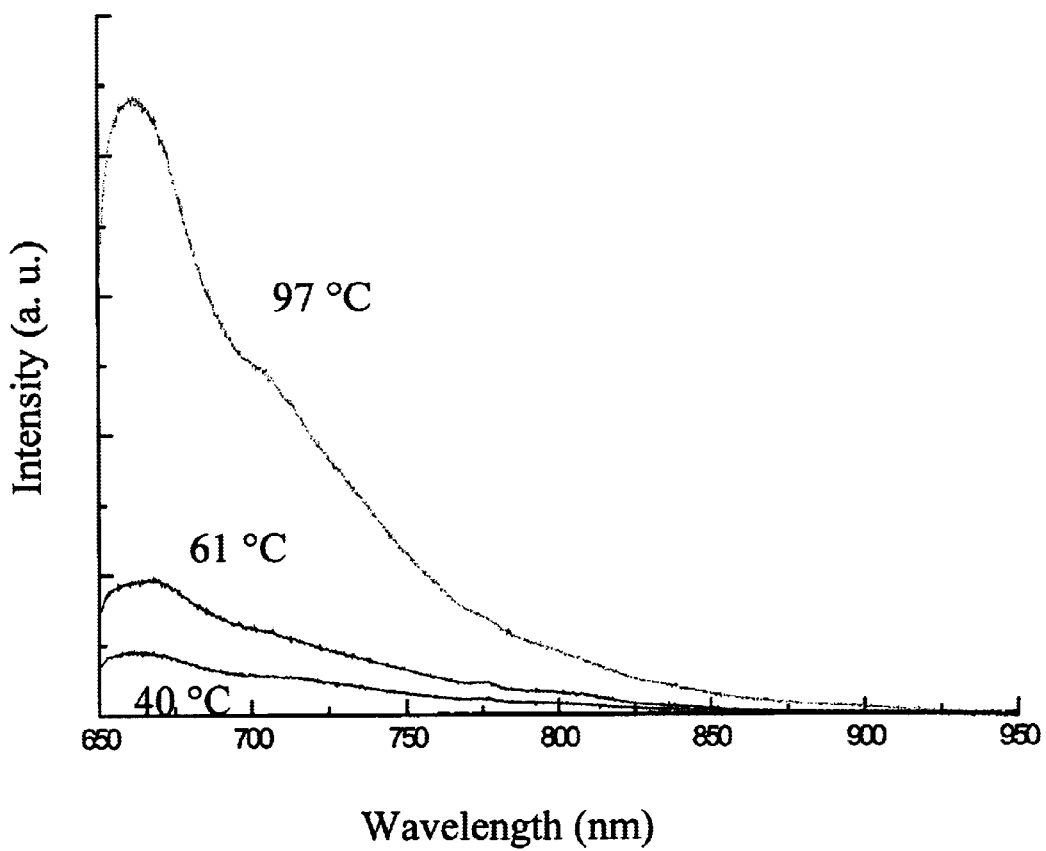
FIG. 6 is a graphic representation of the NIR steady-state emission spectra of tissue samples with different thermal treatment temperatures (40° C., 61 ° C. and 97° C.)

Referring now to FIG. 6, there is shown a graphic representation of the NIR steady-state emission spectra of tissue samples with different thermal treatment temperatures (40° C., 61 ° C. and 97° C.) obtained in the above-described manner. The emission spectral profile was similar for the tissue samples treated at the three temperature levels, the only difference between tissue samples at higher temperature treatment relative to those at lower temperature being stronger emission intensity.

Figure 7:
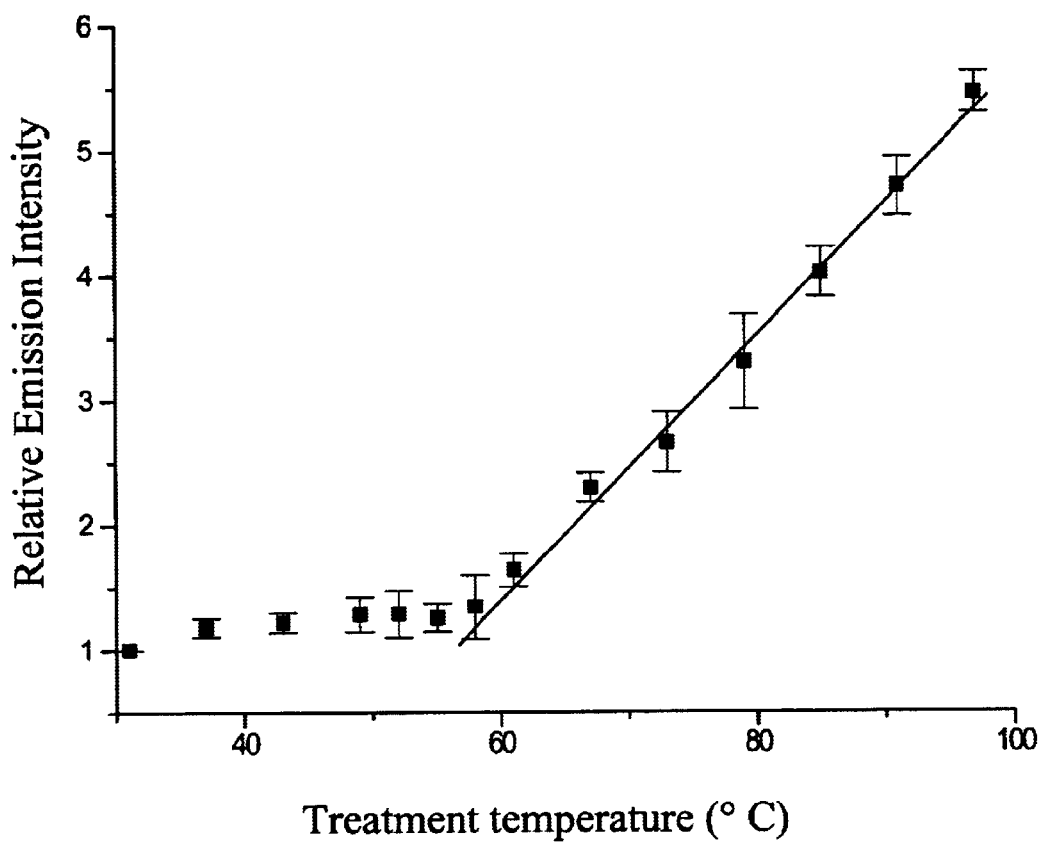
FIG. 7 is a graphic representation of the relative NIR steady-state emissions from thermally treated tissue samples as a function of treatment temperature.

The relationship between the relative emission intensity of the heat-treated samples versus temperature is shown in FIG. 7. Using a linear fitting approach, the intensity of emission was found to be linearly proportional to the temperature treatment of the samples from 55° C. to 97° C. Cancerous and precancerous tissues are hotter and produce a larger wing intensity.

As can readily be appreciated, the above-described relationship could be used for the in vivo monitoring of the local temperature of tissues, for example, to monitor the temperature of tissues involved in laser ablation or laser welding.

Figure 8:
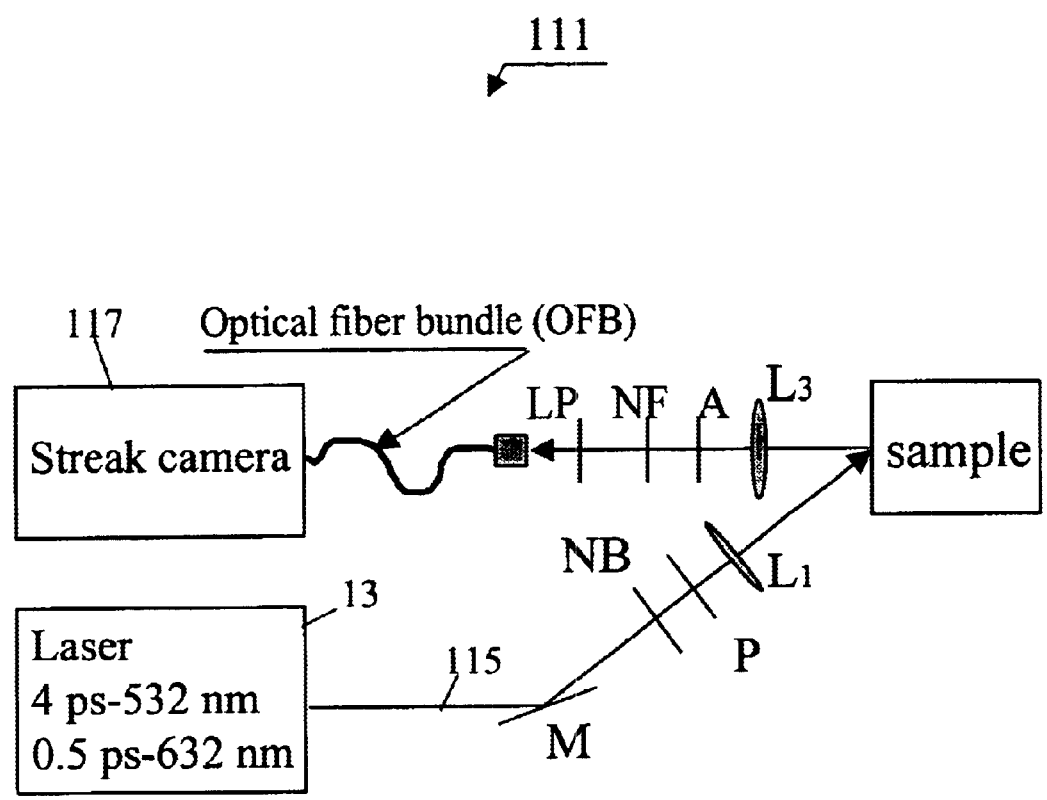
FIG. 8 is a schematic diagram of a second experimental setup used to perform a second embodiment of the method of the present invention.

Referring now to FIG. 8, there is shown a schematic diagram of a second experimental setup used to perform a second embodiment of the method of the present invention, said second experimental setup being constructed according to the teachings of the present invention and being represented by reference numeral 111.

Setup 111 also includes laser system 13 (e.g., 4 ps, 532 nm Nd:YAG laser; 0.5 ps, 632 dye laser) for emitting laser light along a laser path 115. The laser light emitted from system 13 is reflected off mirror M, passed through narrow band filter NB to ensure monochromatic illumination, passed through a polarizer P and focused by lens $L_1$ onto the sample. The light emitted from the tissue sample is collected in a back-scattering geometry using a 3 cm focal length lens $L_3$ and is then passed through an analyzer A, a laser-line notch filter NF to reject the scattered laser light, and a 665 nm long-pass filter LP. The filtered light is then coupled into the input of a streak camera 117 having a spectral response range from the visible to the 1.1 $\mu$m (Hamamatsu Model C1587) using an optical fiber bundle OFB. The output from streak camera 117 is then detected, processed by a computer and displayed. The temporal resolution of system 111 is ~14 ps.

Figure 9A:
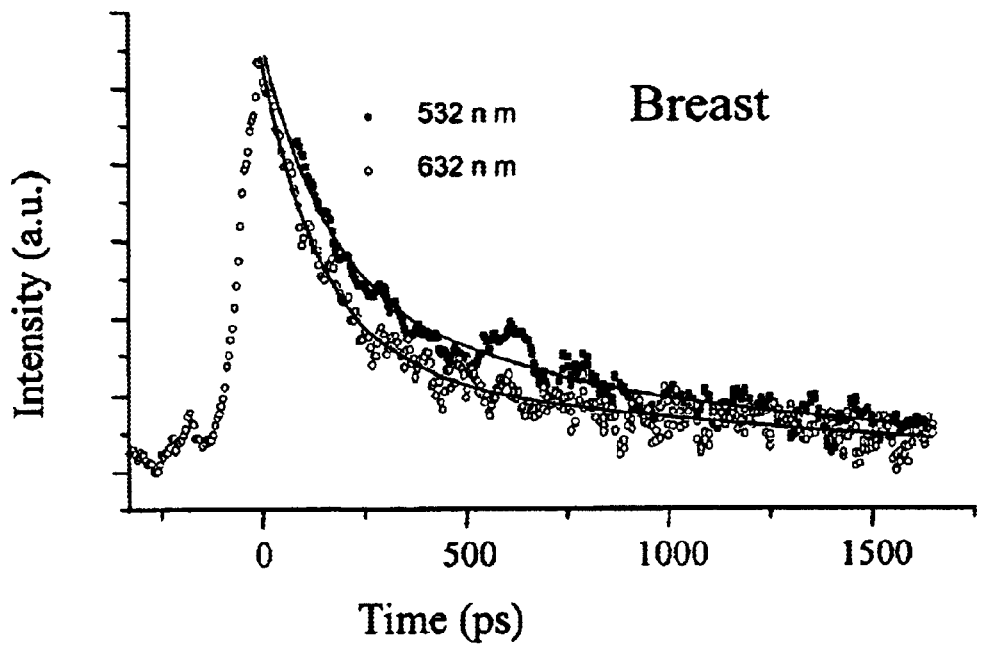
FIGS. 9(a) and 9(b) are graphic representations of the time-resolved emission profiles of the SW emission (beyond 670 nm) under 632 and 532 nm excitation for breast and adipose chicken tissues, respectively.
Figure 9B:
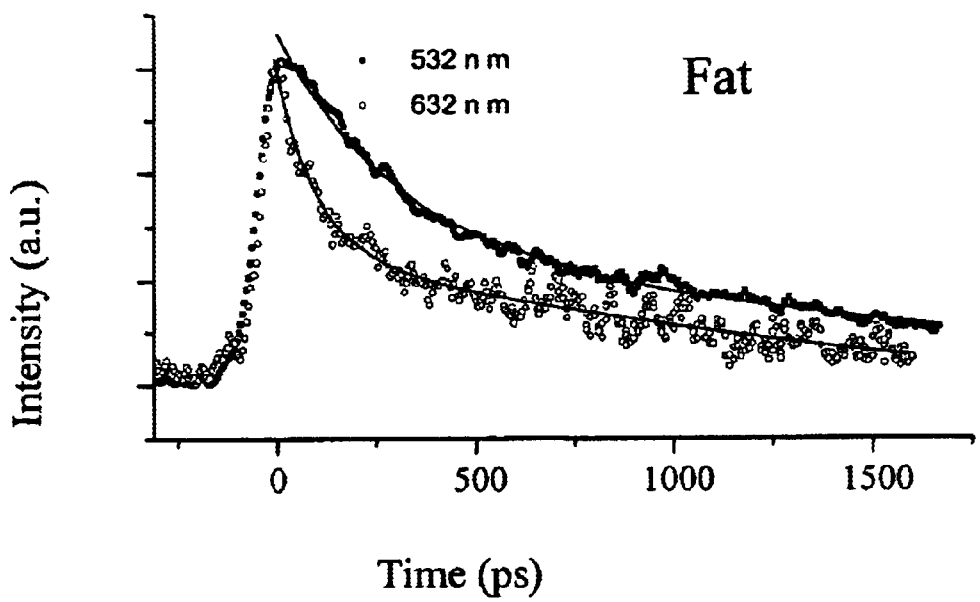

The time-resolved emission profiles of the SW emission (beyond 670 nm) under 632 and 532 nm excitation for breast and adipose chicken tissues are shown in FIGS. 9(a) and 9(b), respectively. As can be seen, the overall decay times of the NIR emission for both adipose and breast chicken tissues are smaller under 632 nm laser excitation than under 532 nm excitation. In addition, the NIR emission decay time for breast chicken tissue is shorter than for adipose tissue under 632 and 532 nm excitations.

The temporal dynamics of the NIR emission is fitted by combination of a rapidly decaying component and a slow component using the following relation:

$$I(t)=A_f\exp(-t/t_f)+A_s\exp(-t/t_s) \qquad (1)$$

where $A_f(A_s)$ is the amplitude and $t_f(t_s)$ is the decay time of the fast(slow) component.

The fitting parameters of the experimental data shown in FIGS. 9(a) and 9(b) obtained using linear square fit to Eq. (1) are summarized in Table I.

TABLE I

| Excitation (nm) | Tissue Type | $t_f$ (ps) | $t_s$ (ns) | $A_f/A_s$ |
| --- | --- | --- | --- | --- |
| 532 | Adipose | 234 ± 25 | 1.51 ± 0.15 | 1.16 ± 0.2 |
| 632 | Adipose | 86 ± 10 | 1.39 ± 0.15 | 1.41 ± 0.2 |

TABLE I-continued

| Excitation (nm) | Tissue Type | $t_f$ (ps) | $t_s$ (ns) | $A_f/A_s$ |
|---|---|---|---|---|
| 532 | Breast | 163 ± 15 | 1.15 ± 0.15 | 1.40 ± 0.2 |
| 632 | Breast | 136 ± 15 | 1.37 ± 0.15 | 2.48 ± 0.3 |

Figure 10A:
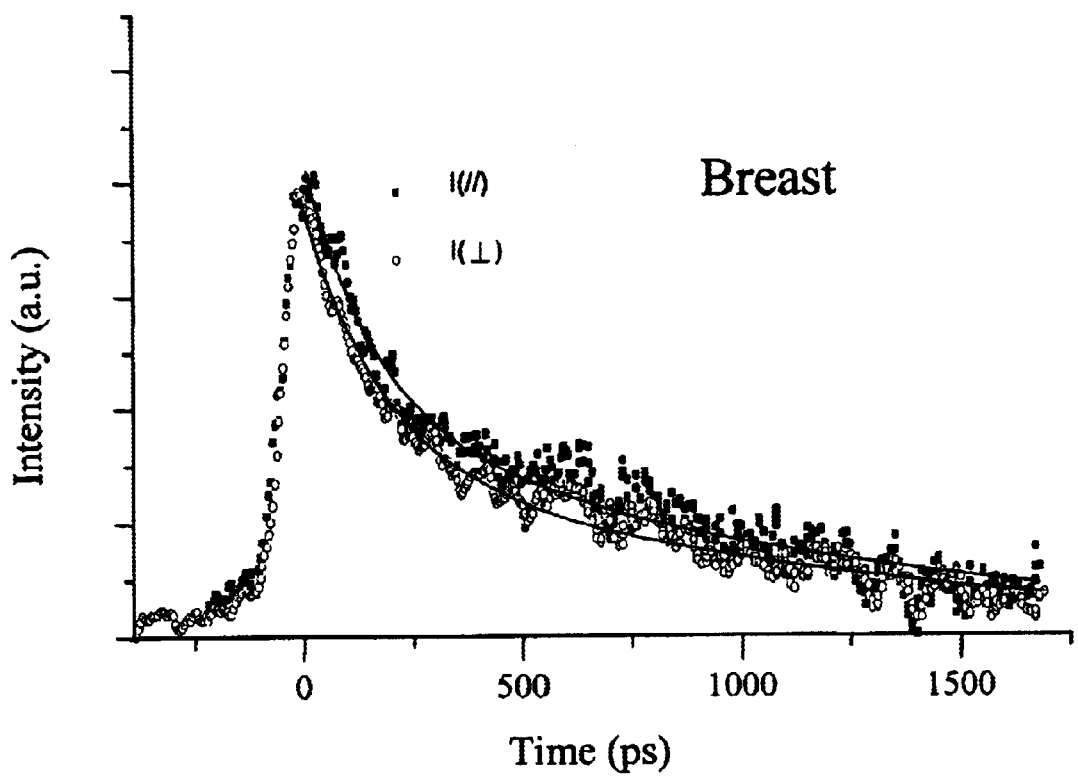
FIGS. 10(a) and 10(b) are graphic representations of the polarized time-resolved profiles of the NIR emission (beyond 670 nm) for breast and adipose chicken tissues, respectively, excited with 532 nm light.
Figure 10B:
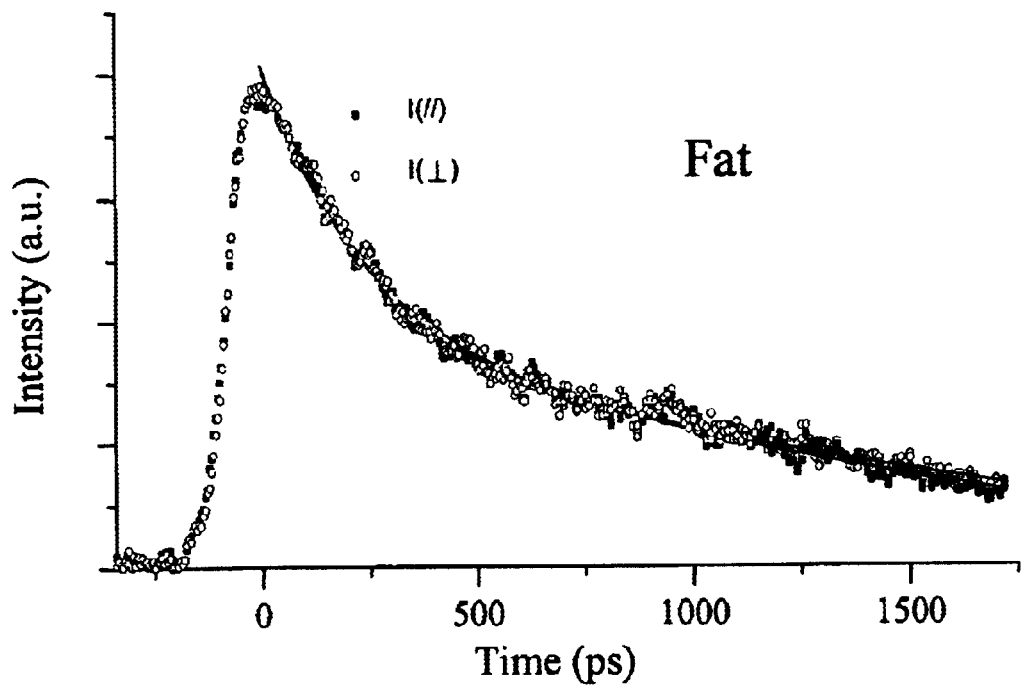
Figure 11A:
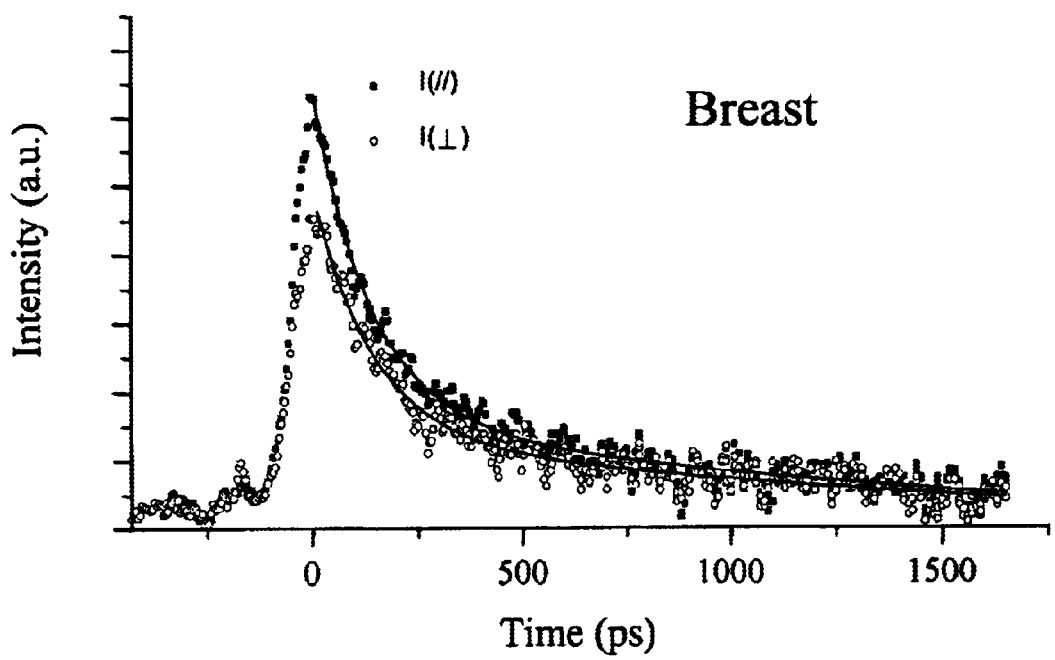
FIGS. 11(a) and 11(b) are graphic representations of the polarized time-resolved profiles of the NIR emission (beyond 670 nm) for breast and adipose chicken tissues, respectively, excited with 632 nm light.
Figure 11B:
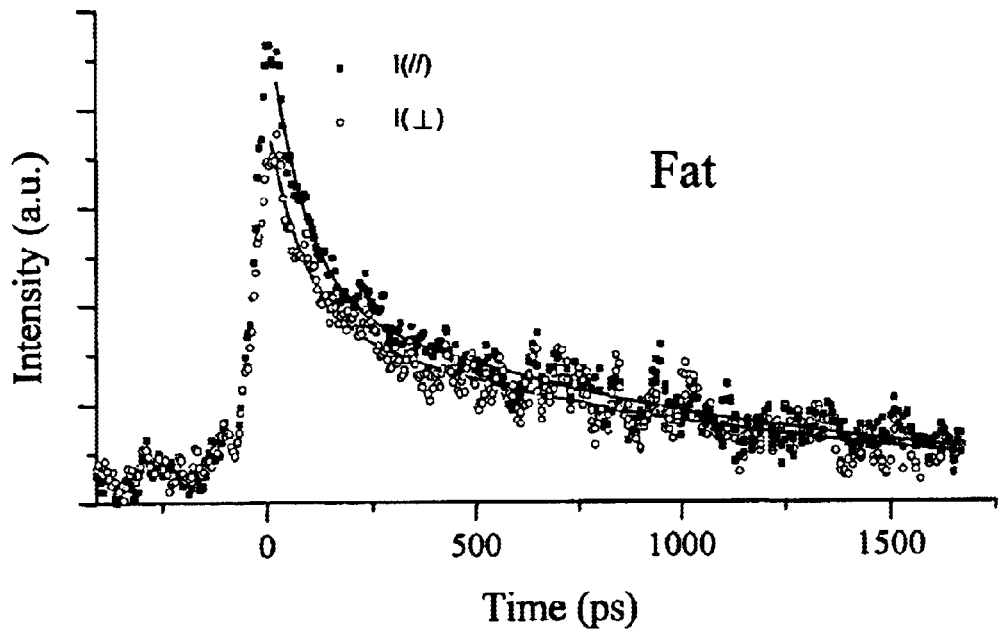

The polarized temporal profiles of the NIR emission (beyond 670 nm) for breast and adipose chicken tissues excited with 532 nm light are shown in FIGS. 10(a) and 10(b), respectively, and the polarized temporal profiles of the NIR emission (beyond 670 nm) for breast and adipose chicken tissues excited with 632 nm light are shown in FIGS. 11(a) and 11(b), respectively. FIG. 10(a) shows that, under 532 nm laser excitation, the parallel component of the emission from breast tissue is slightly stronger than the perpendicular component thereof. The two polarized temporal profiles arising from adipose tissue are approximately equal in intensity (see FIG. 10(b)). FIGS. 11(a) and 11(b) show that the parallel components of the polarized temporal profiles of the NIR emission under 632 nm laser excitation are more intense than the perpendicular components in both types of tissues especially at the early part of the emission.

The fitting parameters of the polarized temporal profiles shown in FIGS. 10(a), 10(b), 11(a) and 11(b) obtained using linear square fit to Eq. (1) are summarized in Table II.

TABLE II

| Excitation (nm) | Polarization | Tissue type | $t_f$ (ps) | $t_s$ (ns) | $A_f/A_s$ |
|---|---|---|---|---|---|
| 532 | Parallel | Adipose | 233 ± 25 | 1.50 ± 0.15 | 1.16 ± 0.2 |
| 532 | Perpend. | Adipose | 236 ± 25 | 1.52 ± 0.15 | 1.16 ± 0.2 |
| 532 | Parallel | Breast | 159 ± 15 | 1.13 ± 0.15 | 1.41 ± 0.2 |
| 532 | Perpend. | Breast | 167 ± 15 | 1.16 ± 0.15 | 1.39 ± 0.2 |
| 632 | Parallel | Adipose | 85 ± 10 | 1.36 ± 0.15 | 1.48 ± 0.2 |
| 632 | Perpend. | Adipose | 88 ± 10 | 1.40 ± 0.15 | 1.37 ± 0.2 |
| 632 | Parallel | Breast | 133 ± 15 | 1.33 ± 0.15 | 2.61 ± 0.3 |
| 632 | Perpend. | Breast | 136 ± 15 | 1.39 ± 0.15 | 2.39 ± 0.3 |

The fitting parameters show that, in all cases, there is a fast decay component ($t_f$) with a relaxtion time on the order of 100–200 ps and a slow decay component ($t_s$) with a relaxation time on the order of 1–1.5 ns. The difference in the temporal profiles of the two polarization components for each type of tissue under 632 nm excitation is reflected in the ratio of the amplitudes $A_f/A_s$ of the fast decay component over the slow decay component.

As noted above in reference to FIGS. 2(a) and 2(b) through 5, there is a clear difference in the intensity of the far-red emission under 632 nm excitation between adipose and breast chicken tissue samples and between cancerous and normal human breast tissue samples. This difference provides a basis for imaging the two types of tissue using their integrated far-red emission intensities.

Figure 12:
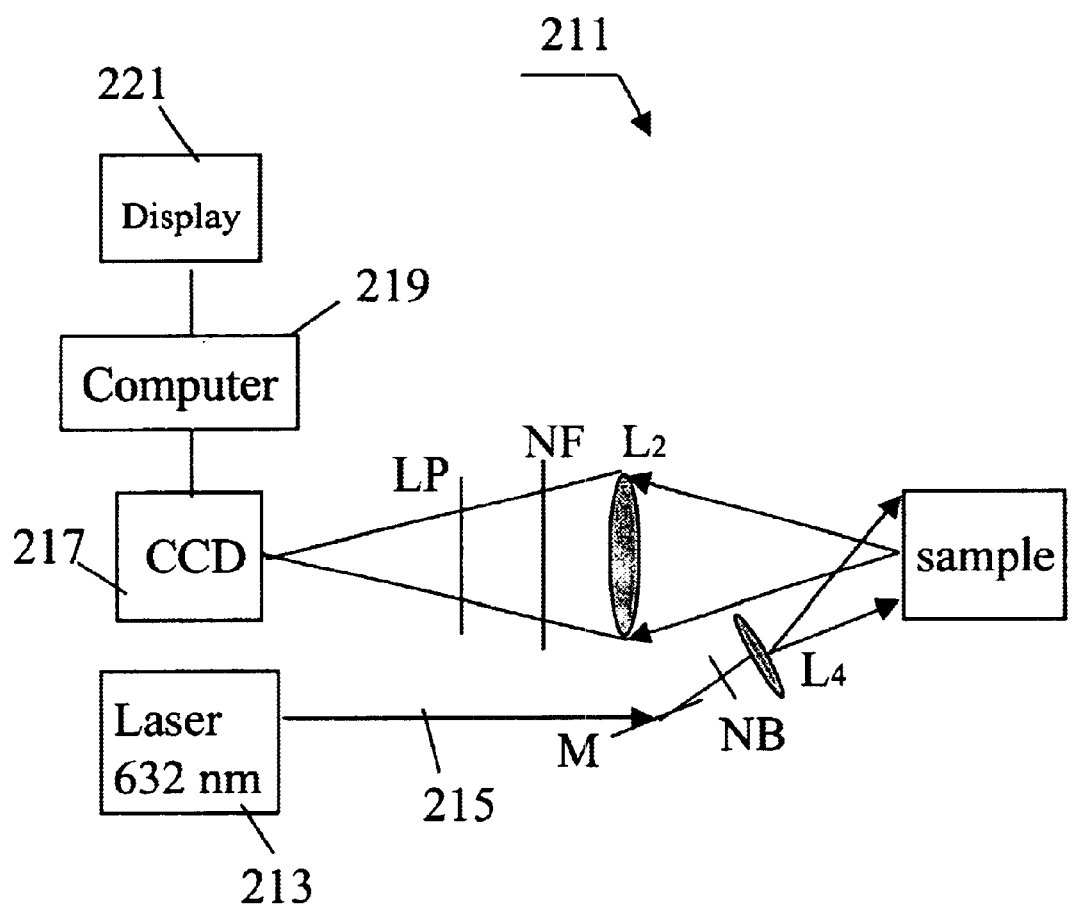
FIG. 12 is a schematic diagram of a first embodiment of an imaging system constructed according to the teachings of the present invention.

Referring now to FIG. 12, there is shown a schematic diagram of a first embodiment of an imaging system that makes use of the aforementioned difference in the integrated far-red emission intensities of different types of tissues, said imaging system being constructed according to the teachings of the present invention and being represented generally by reference numeral 211.

System 211 comprises a laser 213 for emitting laser light along a path 215. In the present embodiment, laser 213 is a 10 mW HeNe laser operating at 632.8 nm. (Laser system 13 may further or alternatively include a single mode 50 mW diode laser operated at 800 nm.) The laser light emitted from system 213 is reflected off mirror M, passed through narrow band filter NB to ensure monochromatic illumination and expanded by a 2 cm focal length lens $L_4$, the central portion of the expanded beam being used to illuminate the tissue sample. The light emitted from the tissue sample is then collected in a back-scattering geometry using 85 mm focal length lens $L_2$, passed through laser-line notch filter NF to reject the scattered laser light, and passed through 665 nm long-pass filter LP. The filtered light is then detected by a cooled CCD camera 217. The output of camera 217 is coupled to a computer 219 for processing, and the output of computer 219 is displayed on a display 221, which may be a monitor and/or a printer.

Figure 13:
FIGS. 13(a) and 13(b) are a pair of images, obtained under room light illumination and using the integrated intensity of NIR emission following illumination at 632 nm, respectively, of a tissue sample consisting of adipose (upper part) and breast (lower part) chicken tissue.
Figure 13:
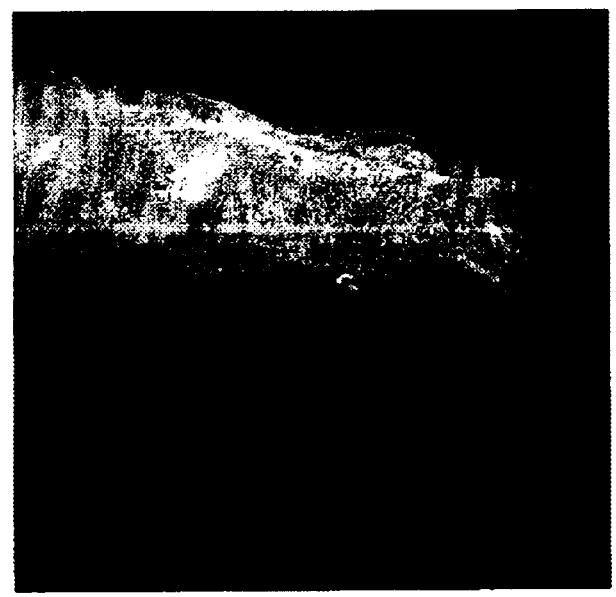

Referring now to FIGS. 13(a) and 13(b), there can be seen a pair of images, obtained under room light illumination and using system 211, respectively, of a tissue sample consisting of adipose (upper part) and breast (lower part) chicken tissue. As can be seen in FIG. 13(b), the adipose section of the tissue sample appears to be much brighter than the breast section of the tissue sample, thereby allowing for clear discrimination of the two sections based on tissue type.

Figure 14:
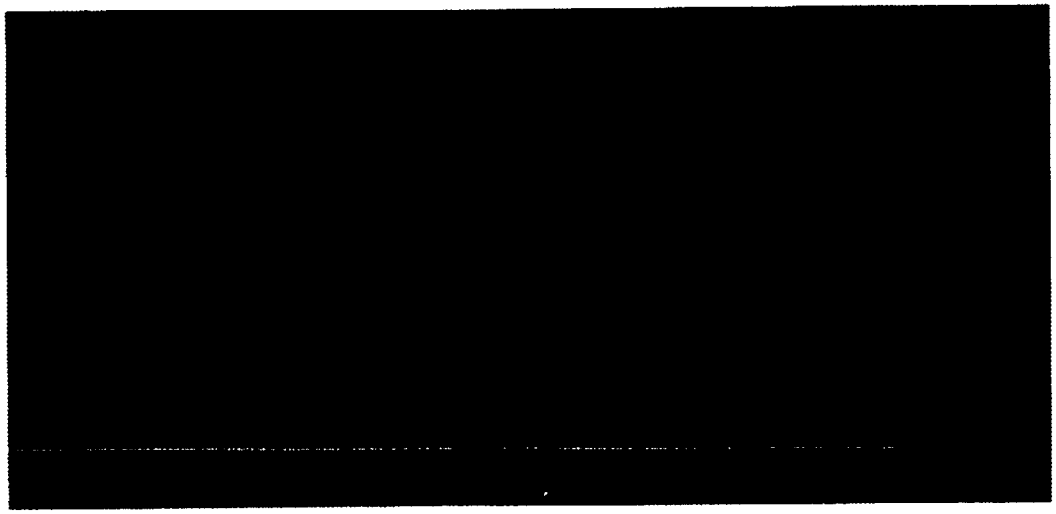
FIGS. 14(a) and 14(b) are a pair of images, obtained under room light illumination and using the integrated intensity of NIR emission following illumination at 632 nm, respectively, of normal (left) and cancerous (right) human breast tissue samples.
Figure 14:
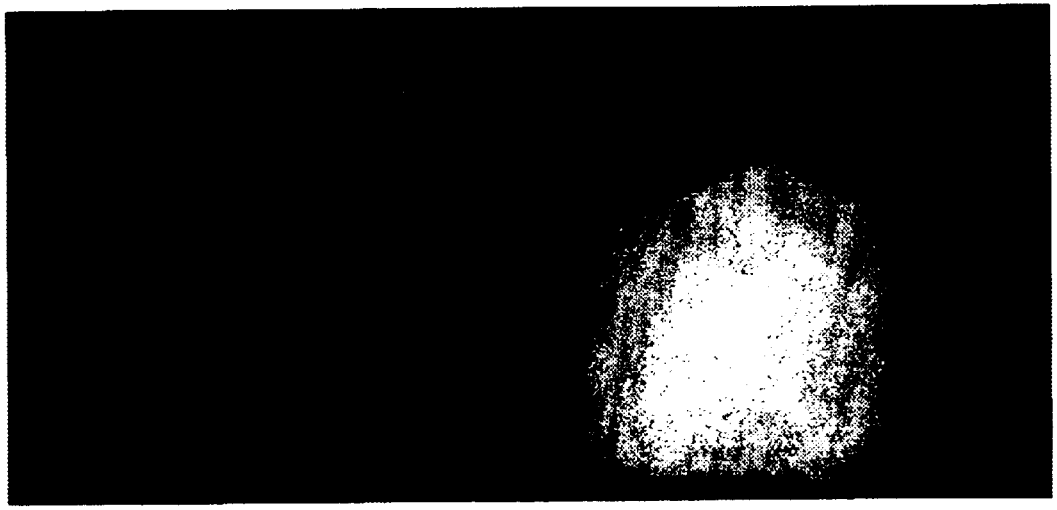

Referring now to FIGS. 14(a) and 14(b), there can be seen a pair of images, obtained under room light illumination and using the integrated intensity of NIR emission following illumination at 632 nm, respectively, of normal (left) and cancerous (right) human breast tissue samples. As can be seen in FIG. 14(b), the cancer tissue sample appears as a brighter "object" than the normal tissue sample. This result occurred in 10 out of 12 sample pairs tested.

As can be seen, the aforementioned shadowgrams obtained using the far-red and NIR emission resulting from red or infrared photoexcitation can be used to characterize the condition of a tissue. This technique can be applied to the imaging of tissues located inside the human body (such tissues including oral, colon, prostate, mucosa, bladder, GI tract, cervix, uterus, brain, GYN tract, lung or skin) using various endoscopic imaging techniques and/or optical needle fibers. The utilization of red or infrared illumination for excitation in combination with spectral wing emission for image formation provides a number of benefits, particularly in a clinical environment, as it enables the in vivo, in situ, non-invasive measurement of tissues, without requiring removal of tissues. Using red light or infrared light for illumination, deeper photon penetration is achieved and the image obtained may contain information regarding tissue structures located underneath the surface of the tissue under investigation.

Figure 15:
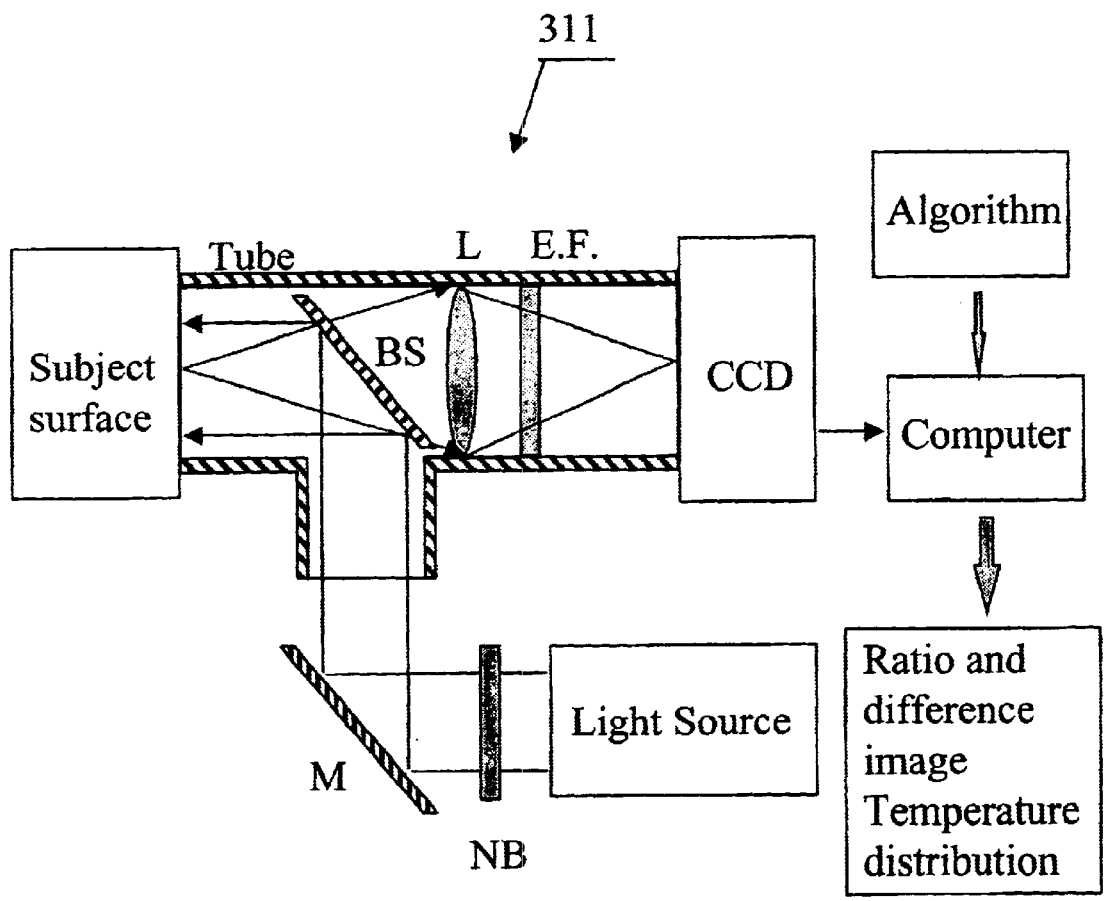
FIG. 15 is a schematic diagram of a second embodiment of an imaging system constructed according to the teachings of the present invention.

Referring now to FIG. 15, there is shown a schematic diagram of a second embodiment of an imaging system constructed according to the teachings of the present invention, said imaging system being represented generally by reference numeral 311.

In system 311, the illumination beam from a laser source is first passed through a laser-line narrow-band filter NB to ensure monochromatic irradiation of at least 600 nm and is then directed into a tube using a mirror M. (Instead of using a laser, a lamp with a narrow band filter can be used to select a desired illumination wavelength of at least 600 nm.) The illumination beam is then reflected off a beam splitter BS onto the subject surface. The far-red and/or NIR emission from the sample is then transmitted through beam splitter BS, collected by a lens L or other equivalent optical component, and passed through one or more wavelength selective filters of an emission filter wheel EF. (Elastic light intensity scattered at $\lambda_1$ can be used as a reference for setting up ratios or differences at a pair of emission wavelengths.) The filtered light at $\lambda_2$, $\lambda_3$, etc. is then detected by a CCD camera. The output from the CCD camera is then processed by a computer using an algorithm and is used to provide an image of the sample. The spatial profile of the illumination beam at the sample may be measured and may be used to normalize the intensity of the emission image. The relative NIR intensity gives information about the state of the tissue sample.

Figure 16:
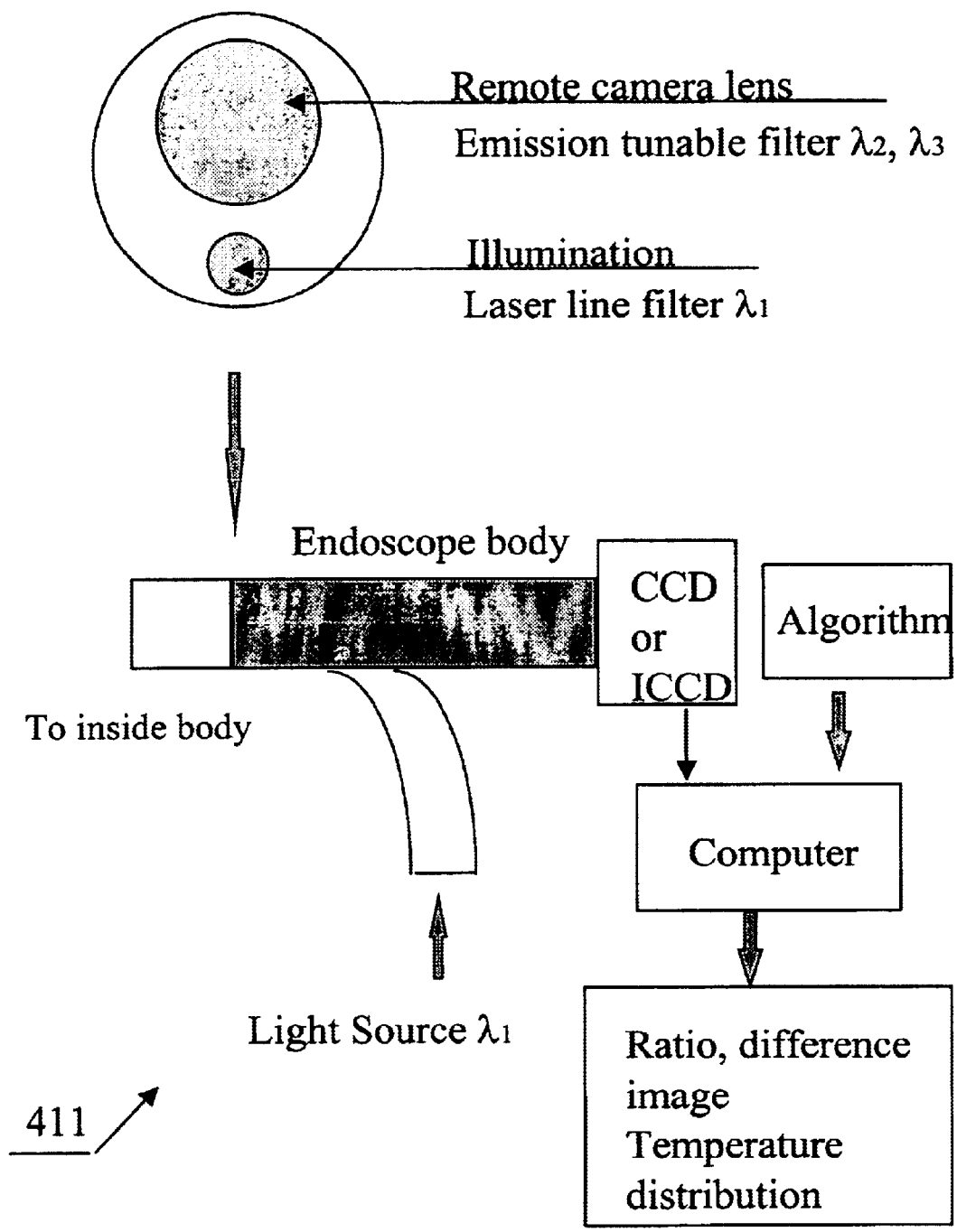
FIG. 16 is a schematic diagram of a third embodiment of an imaging system constructed according to the teachings of the present invention.

An analogous imaging system incorporated into an endoscope is schematically depicted in FIG. 16 and is represented therein by reference numeral 411. In system 411, the laser source (operating from 650 to 900 nm) is coupled into the illumination channel of the endoscope to deliver by the appropriate means (usually a fiber), the excitation light into the designated part of the body. At the output of the illumination carrying channel, there is laser-line narrow band filter or other equivalent means for ensuring monochromatic photoexcitation of the sample. The far-red to NIR emission image is collected by the endoscope after passing through the emission filter and coupled into the CCD camera. The emission filters are positioned before or after the image collection optics at the tip of the endoscope and may include a laser line notch filter and a long pass filter or equivalent means to reject the scattered laser light from the sample's surface and to select the emitted light to be used for imaging. For the selected different SW emission wavelengths range, the emission filters could be used with liquid crystal or acoustic optical tunable filters or thin filters inside mechanical filter wheel controlled by computer to change the measurement wavelengths to the required wavelength positions.

To reduce the intensity error generated by the laser illumination, the back scattering image will be obtained from a standard scattering sample because the illumination intensity distribution will be used on the measurement of the background image ($I_0$). The far-red SW emission spatial (x,y) images ($I_{02}$, $I_{03}$, . . . ) obtained through different emission filters ($\lambda_2$, $\lambda_3$, . . . ) respectively and the back scattering image ($I_{01}$) over the (x,y) field will be obtained without filtering. The normalized far-red emission image will be the ratio between image obtained through different emission filters and illumination intensity distribution image: $I_2(x,y)=I_{02}/I_0$, $I_3(x,y)=I_{03}/I_0$, . . . and similarly, the normalized back scattering image will be $I_1(x,y)=I_{01}$, $I_0$. From the normalized data set, spatial ratio images can be formed and defined as $$R_{23}(x,y)=I_2(x,y)/I_3(x,y),$$

and/or the difference images can be defined as $$D_{23}(x,y)=I_2(x,y)-I_3(x,y).$$

These images will be used for different tissue classification purposes.

The SW shadowgrams obtained using the imaging systems of FIGS. 15 and 16 or equivalent can provide information on the location and status of various tissue types over a spatial region. In a clinically relevant environment, medical personnel will be able to quickly utilize these images to better assess the physiological condition of a patient's tissue in vivo.

From the teaching of the relationship between the intensity of SW emission and the extent of thermal damage of tissue or tissue temperature described above, the systems of FIGS. 15 and 16 can also be used to monitor the extent of thermal damage or local temperature distribution within a tissue. Before laser welding or ablation surgery, tissue temperature is at the regular body temperature, and the intensity distribution can be used as a measurement baseline.

During welding or ablation, the intensity of the SW emission from the tissue will change to a certain level depending on the extent of thermal damage at the tissue or tissue temperature. From the above-described relationship between the intensity change and temperature, the extent of thermal damage or temperature distribution can be calculated and displayed.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for characterizing the condition of a native tissue sample as being one of normal, benign, precancerous and cancerous, said method comprising the steps of:
   (a) photoexciting the native tissue sample with substantially monochromatic light having a wavelength of at least 600 nm, whereby a far red and near infrared spectral wing emission is emitted from the native tissue sample; and
   (b) using at least the far red and near infrared spectral wing emission emitted from the native tissue sample to characterize the condition of the native tissue sample as being one of normal, benign, precancerous and cancerous.

2. The method as claimed in claim 1 wherein the substantially monochromatic photoexciting light is a continuous beam of light, wherein said native far red and near infrared spectral wing emission from the tissue sample includes native steady-state far red and near infrared spectral wing emission and wherein said using step comprising using said native steady-state far red and near infrared spectral wing emission emitted from the tissue sample to characterize the condition of the tissue sample.

3. The method as claimed in claim 2 wherein the substantially monochromatic photoexciting light has a wavelength in the range of about 600 to 980 nm and wherein said native steady-state far red and near infrared spectral wing emission has a wavelength of at least 20 nm greater than said substantially monochromatic photoexciting light.

4. The method as claimed in claim 3 wherein the substantially monochromatic photoexciting light has a wavelength of about 632 nm and wherein said native steady-state far red and near infrared spectral wing emission wavelengths are 650 nm to 950 nm.

5. The method as claimed in claim 3 wherein the substantially monochromatic photoexciting light has a wavelength of about 800 nm and wherein said native steady-state far red and near infrared spectral wing emission wavelengths are 840 to 950 nm.

6. The method as claimed in claim 2 wherein said using step comprises obtaining a spectral profile of the spectral wing emission emitted from the tissue sample and comparing said spectral profile to standards obtained from tissues whose conditions are known over wavelengths greater than 750 nm.

7. The method as claimed in claim 6 wherein said using step comprises determining a normalized integrated intensity of the spectral profile and comparing said normalized integrated intensity to appropriate standards.

8. The method as claimed in claim 6 wherein said using step comprises determining a ratio or difference of intensities at two wavelengths along said spectral profile and comparing said ratio or difference to appropriate standards.

9. The method as claimed in claim 2 wherein said using step comprises detecting the native steady-state far red and near infrared spectral wing at two wavelengths, determining a ratio or difference of intensities at said two wavelengths and comparing said ratio or difference to appropriate standards.

10. The method as claimed in claim 1 wherein the substantially monochromatic photoexciting light is a light pulse and wherein said using step comprises using the resultant time-resolved native fluorescence emitted from the native tissue sample to characterize the condition of the native tissue sample.

11. The method as claimed in claim 10 wherein the substantially monochromatic photoexciting light has a wavelength in the range of about 600 to 980 nm and wherein said native time-resolved fluorescence has a wavelenghth greater than 20 nm than said substantially monochromatic photoexciting light.

12. The method as claimed in claim 11 wherein the substantially monochromatic photoexciting light has a wavelength of about 632 nm and wherein said native time-resolved fluorescence has a wavelength in the range of 650 to 950 nm.

13. The method as claimed in claim 10 wherein the substantially monochromatic photoexciting light is produced by a diode laser.

14. The method as claimed in claim 10 wherein said using step comprises obtaining a profile of the time-resolved spectral wing emitted from the native tissue sample and comparing said profile to standards obtained from tissues whose conditions are known.

15. The method as claimed in claim 14 wherein said comparing step comprises fitting the profile to the formula $I(t)=A_1 e^{(-t/\tau 1)}+A_2 e^{(-t/\tau 2)}$ and comparing the resultant values for at least one of $A_1/A_2$ and $\tau_1$ with appropriate standards.

16. The method as claimed in claim 1 wherein the substantially monochromatic photoexciting light is a polarized light pulse and wherein said using step comprises using at least one of the parallel and perpendicular components of the resultant polarized time-resolved spectral wing emitted from the native tissue sample to characterize the condition of the native tissue sample.

17. The method as claimed in claim 16 wherein the substantially monochromatic photoexciting light has a wavelength in the range of about 600 to 980 nm and wherein said far red and near infrared spectral wing emission has a wavelength greater than 20 nm than the substantially monochromatic photoexciting light.

18. The method as claimed in claim 17 wherein the substantially monochromatic photoexciting light has a wavelength of about 632 nm and wherein said far red and near infrared spectral wing emission has a wavelength from 650 nm to 950 nm.

19. The method as claimed in claim 16 wherein said using step comprises obtaining a profile of at least one of the parallel and perpendicular components and comparing said profile(s) to standards obtained from tissues whose conditions are known.

20. The method as claimed in claim 1 wherein the tissue sample is a human tissue sample.

21. The method as claimed in claim 20 wherein the tissue sample is selected from the group consisting of the colon, mucosa, prostate, bladder, GI tract, cervix, uterus, GYN tract, brain, lung, bronchus and skin.

22. The method as claimed in claim 20 wherein the method is used to diagnose the breast cancer from normal human breast tissue from SW emission wavelength profiles.

23. A method for diagnosing Alzheimer's disease in human brain tissues said method comprising the steps of:
  (a) photoexciting the native human tissue sample with substantially monochromatic light having a wavelength of at least 600 nm, whereby a far red and near infrared spectral wing emission is emitted from the native human tissue sample; and
  (b) using at least the far red and near infrared spectral wing emission emitted from the native human tissue sample to diagnose Alzheimer's disease in the native human tissue sample.

24. A method for diagnosing diabetes disease in native human tissues said method comprising the steps of:
  (a) photoexciting the native human tissue sample with substantially monochromatic light having a wavelength of at least 600 nm, whereby a far red and near infrared spectral wing emission is emitted from the native human tissue sample; and
  (b) using at least the far red and near infrared spectral wing emission emitted from the native human tissue sample to diagnose diabetes disease in the native human tissue sample.

25. A method for imaging a native tissue sample, said method comprising the steps of.
  (a) photoexciting the native tissue sample with substantially monochromatic light having a wavelength of at least 600 nm, whereby a far red and near infrared spectral wing emission is emitted from the native tissue sample; and
  (b) using at least the far red and near infrared spectral wing emission emitted from the native tissue sample to form an image of the native tissue sample.

26. The method as claimed in claim 25 wherein the substantially monochromatic photoexciting light has a wavelength in the range of about 600 to 980 nm and wherein said native fluorescence has a wavelength of at least 20 nm more than said substantially monochromatic photoexciting light.

27. The method as claimed in claim 25 further comprising the step of using the image of the native tissue sample to characterize the condition of the imaged native tissue sample.

28. An apparatus for imaging a native tissue sample, said apparatus comprising:
  (a) a light source for photoexciting the native tissue sample with substantially monochromatic light having a wavelength of at least 730 nm;
  (b) a light detector;
  (c) collection optics for imaging the light emitted from the native tissue sample onto the light detector;
  (d) filter means positioned between the native tissue sample and the light detector for selectively transmitting, from the light emitted from the native tissue sample, light having a wavelength greater than said substantially monochromatic light at least 20 nm greater than excitation wavelength; and
  (e) a display coupled to said light detector for displaying an image of the native tissue sample based on the light detected by said light detector.

29. The apparatus as claimed in claim 28 wherein said light source emits substantially monochromatic light having a wavelength in the range of about 600 to 980 nm and emissions of spectral wing at wavelengths greater than 20 nm from excitation wavelength.

30. The apparatus as claimed in claim 28 wherein said light source is selected from the group consisting of a laser and the combination of a lamp and a narrow band filter.

31. The apparatus as claimed in claim 30 wherein said light source is a laser.

32. The apparatus as claimed in claim 28 wherein said light detector is selected from the group consisting of a CCD camera, a photomultiplier and a photodiode.

33. The apparatus as claimed in claim 32 wherein said light detector is a CCD camera.

34. The apparatus as claimed in claim 28 wherein said filter means comprises a filter selected from the group consisting of a bandpass filter, a long wavelength pass filter and a narrow band filter.

35. The apparatus as claimed in claim 28 wherein said filter means comprises a filter wheel and a plurality of filters, each of said filters being selective for a different emission wavelength.

36. The apparatus as claimed in claim 28 further comprising an endoscope for use in transmitting light from said light source to the tissue sample and for use in transmitting light from the tissue sample to said light detector.

37. The apparatus as claimed in claim 28 further comprising means for characterizing the condition of the native tissue sample.

* * * * *